(12) United States Patent
Kovi et al.

(10) Patent No.: US 9,988,389 B2
(45) Date of Patent: Jun. 5, 2018

(54) PROCESSES FOR MAKING PONATINIB AND INTERMEDIATES THEREOF

(71) Applicant: Apicore US LLC, Somerset, NJ (US)

(72) Inventors: Ravishanker Kovi, Monroe, NJ (US);
Jayaraman Kannapan, Gujarat (IN);
Sanjay F. Thakor, Gujarat (IN);
Ashish Naik, Piscataway, NJ (US);
Dhakhada Chetana Bharatbhai,
Gujarat (IN); Khichi Kuldip Fatehlal,
Gujarat (IN); Shivnath Sahebrao Patil,
Dhule (IN)

(73) Assignee: Apicore US LLC, Somerset, NJ (US)

( * ) Notice: Subject to any disclaimer, the term of this patent is extended or adjusted under 35 U.S.C. 154(b) by 0 days. days.

(21) Appl. No.: 15/178,813

(22) Filed: Jun. 10, 2016

(65) Prior Publication Data
US 2016/0362411 A1 Dec. 15, 2016

Related U.S. Application Data

(60) Provisional application No. 62/174,083, filed on Jun. 11, 2015, provisional application No. 62/175,721, filed on Jun. 15, 2015, provisional application No. 62/204,571, filed on Aug. 13, 2015.

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| 2007/0191376 A1 | 8/2007 | Zou | |
|---|---|---|---|
| 2013/0053370 A1 | 2/2013 | Son | |
| 2014/0343282 A1* | 11/2014 | Kovi et al. | C07D 487/04 544/236 |

FOREIGN PATENT DOCUMENTS

| WO | 2004108699 A1 | 12/2004 | |
| WO | WO 2004108699 | * 12/2004 | C07D 401/04 |

OTHER PUBLICATIONS

International Search Report and Written Opinion for corresponding PCT application No. PCT/2016/36857, 9 pages, dated Sep. 7, 2016.
Gamble, et al. "Aryl Nitro Reduction with Iron Powder or Stannous Chloride under Ultrasonic Irradiation", Synthetic Communications, 37,2007, 2777-2786; University of Wollongong—Research Online, pp. 1-12 (2007).

* cited by examiner

*Primary Examiner* — Paul V Ward

(57) ABSTRACT

Methods are disclosed for making 3-(imidazo[1,2-b]pyridazin-3-ylethynyl)-4-methyl-N-[4-[(4-methylpiperazin-1-yl)methyl]-3-(trifluoromethyl)phenyl]benzamide, intermediates and pharmaceutically acceptable salts thereof.

7 Claims, No Drawings

PROCESSES FOR MAKING PONATINIB AND INTERMEDIATES THEREOF

CROSS-REFERENCE TO RELATED APPLICATIONS

This application claims the benefit of each of U.S. Provisional Patent Application Ser. No. 62/174,083 filed Jun. 11, 2015, U.S. Provisional Patent Application Ser. No. 62/175,721 filed Jun. 15, 2015, and U.S. Provisional Patent Application Ser. No. 62/204,571 filed Aug. 13, 2015, the entireties of which are incorporated herein by reference.

FIELD OF THE INVENTION

The presently disclosed subject matter provides novel synthetic approaches to make 3-(imidazo[1,2-b]pyridazin-3-ylethynyl)-4-methyl-N-[4-[(4-methylpiperazin-1-yl)methyl]-3-(trifluoromethyl)phenyl]benzamide, intermediates and pharmaceutically acceptable salts thereof.

BACKGROUND 3-(imidazo[1,2-b]pyridazin-3-ylethynyl)-4-methyl-N-[4-[(4-methylpiperazin-1-yl)methyl]-3-(trifluoromethyl)phenyl]benzamide, also known as ponatinib, is a multi-targeted tyrosine-kinase inhibitor used in the treatment of chronic myeloid leukemia (CML) and Philadelphia chromosome positive (Ph+) acute lymphoblastic leukemia (ALL). Some forms of CML, those that have the T315I mutation, are resistant to current therapies such as imatinib. Ponatinib was designed to be effective against these types of tumors.

SUMMARY OF THE INVENTION

The presently disclosed processes involve a novel synthetic approach to make ponatinib in a simple and easily scalable process, overcoming the drawbacks of prior art processes.

In one embodiment a method is disclosed for the production of ponatinib hydrochloride of the formula (I)

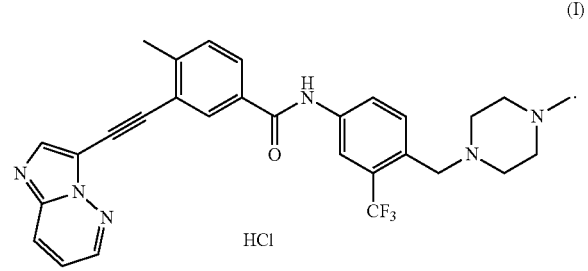 [SMILES: Cc1ccc(C(=O)Nc2ccc(CN3CCN(C)CC3)c(C(F)(F)F)c2)cc1C#Cc1cnc2cccnn12 ; Cl]

In accordance with one or more embodiments, a method of making ponatinib or a pharmaceutically acceptable salt thereof, includes the steps of: reacting 3-iodo-4-methylbenzoyl chloride with a solution of 4-amino-2-(trifluoromethyl) benzaldehyde to obtain N-(4-formyl-3-(trifluoromethyl)phenyl)-3-iodo-4-methylbenzamide; adding a base, an iodide reagent and a catalyst to a solution of N-(4-formyl-3-(trifluoromethyl)phenyl)-3-iodo-4-methylbenzamide to obtain a reaction mixture, and adding 3-ethynylimidazo[1,2-b]pyridazine to the reaction mixture to obtain N-(4-formyl-3-(trifluoromethyl)-phenyl)-3-(imidazo[1,2-b]pyridazin-3-ylethynyl)-4-methylbenzamide; reacting a solution of N-(4-formyl-3-(trifluoromethyl)-phenyl)-3-(imidazo[1,2-b]pyridazin-3-ylethynyl)-4-methylbenzamide with sodium borohydride to obtain N-(4-(hydroxymethyl)-3-(trifluoromethyl)-phenyl)-3-(imidazo[1,2-b]pyridazin-3-ylethynyl)-4-methylbenzamide; reacting a solution of N-(4-(hydroxymethyl)-3-(trifluoromethyl)-phenyl)-3-(imidazo[1,2-b]pyridazin-3-ylethynyl)-4-methylbenzamide with a chloride to obtain N-(4-(chloromethyl)-3-(trifluoromethyl)phenyl)-3-(imidazo[1,2-b]pyridazin-3-ylethynyl)-4-methylbenzamide; and reacting a solution of N-(4-(chloromethyl)-3-(trifluoromethyl)phenyl)-3-(imidazo[1,2-b]pyridazin-3-ylethynyl)-4-methylbenzamide with N-methylpiperazine to obtain 3-(imidazo[1,2-b]pyridazin-3-ylethynyl)-4-methyl-N-(4-((4-methylpiperazin-1-yl)methyl)-3-(trifluoromethyl)phenyl)benzamide.

Ponatinib hydrochloride may be obtained by the further step of saturating a solution of the 3-(imidazo[1,2-b]pyridazin-3-ylethynyl)-4-methyl-N-(4-((4-methylpiperazin-1-yl)methyl)-3-(trifluoromethyl)phenyl)benzamide with HCl gas.

Suitable solvents for dissolving 4-amino-2-(trifluoromethyl) benzaldehyde include but are not limited to dichloromethane (MDC) and ethyl acetate. In one embodiment the solvent is MDC.

Suitable solvents for dissolving N-(4-formyl-3-(trifluoromethyl)phenyl)-3-iodo-4-methylbenzamide include but are not limited to dimethylformamide (DMF), dimethyl sulfoxide (DMSO), tetrahydrofuran (THF) and acetonitrile. Suitable bases for addition to a solution of N-(4-formyl-3-(trifluoromethyl)phenyl)-3-iodo-4-methylbenzamide include but are not limited to N,N-diisopropylethylamine (DIPEA), triethylamine (TEA) and diethylamine (DEA). In one embodiment the base is DIPEA.

An example of a suitable iodide reagent for addition to a solution of N-(4-formyl-3-(trifluoromethyl) phenyl)-3-iodo-4-methylbenzamide is CuI.

Suitable catalysts for addition to a solution of N-(4-formyl-3-(trifluoromethyl)phenyl)-3-iodo-4-methylbenzamide include but are not limited to $PdCl_2(PPh_3)_2$, $Pd(PPh_3)_4$, $Pd(dppe)Cl$, $Pd(dppp)Cl_2$, and $Pd(dppf)Cl_2$. In one embodiment the catalyst is $PdCl_2(PPh_3)_2$.

Exemplary chloride compounds for reacting with a solution of N-(4-(hydroxymethyl)-3-(trifluoromethyl)-phenyl)-3-(imidazo[1,2-b]pyridazin-3-ylethynyl)-4-methylbenzamide include but are not limited to phosphoryl chloride, thionyl chloride, oxalyl chloride, cyanuric chloride and phosphorous pentachloride. In certain embodiments the chloride compound is phosphoryl chloride or thionyl chloride.

In accordance with some embodiments the 4-amino-2-(trifluoromethyl)benzaldehyde may be obtained by reacting a solution of 4-nitro-2-(trifluoromethyl)benzaldehyde in AcOH with iron.

In still further embodiments, methods of making ponatinib or a pharmaceutically acceptable salt thereof, may include the steps of reacting N-(4-(hydroxymethyl)-3-(trifluoromethyl)-phenyl)-3-(imidazo[1,2-b]pyridazin-3-ylethynyl)-4-methylbenzamide with a chloride compound to obtain N-(4-(chloromethyl)-3-(trifluoromethyl)phenyl)-3-(imidazo[1,2-b]pyridazin-3-ylethynyl)-4-methylbenzamide; and adding N-methylpiperazine to a solution of N-(4-(chloromethyl)-3-(trifluoromethyl)phenyl)-3-(imidazo[1,2-b]pyridazin-3-ylethynyl)-4-methylbenzamide to obtain 3-(imidazo[1,2-b]pyridazin-3-ylethynyl)-4-methyl-N-(4-((4-methylpiperazin-1-yl)methyl)-3-(trifluoromethyl)phenyl)benzamide.

Ponatinib hydrochloride may be obtained by the further step of saturating a solution of the 3-(imidazo[1,2-b]pyridazin-3-ylethynyl)-4-methyl-N-(4-((4-methylpiperazin-1-yl)methyl)-3-(trifluoromethyl)phenyl)benzamide with HCl gas.

Exemplary chloride compounds include but are not limited to phosphoryl chloride, thionyl chloride, oxalyl chloride, cyanuric chloride and phosphorous pentachloride. In certain embodiments the chloride is phosphoryl chloride or thionyl chloride.

In further embodiments, the step of reacting N-(4-(hydroxymethyl)-3-(trifluoromethyl)-phenyl)-3-(imidazo[1,2-b]pyridazin-3-ylethynyl)-4-methylbenzamide with a chloride compound to obtain N-(4-(chloromethyl)-3-(trifluoromethyl)phenyl)-3-(imidazo[1,2-b]pyridazin-3-ylethynyl)-4-methylbenzamide may include adding thionyl chloride to a solution of N-(4-(hydroxymethyl)-3-(trifluoromethyl)-phenyl)-3-(imidazo[1,2-b]pyridazin-3-ylethynyl)-4-methylbenzamide.

In still further embodiments, the step of reacting N-(4-(hydroxymethyl)-3-(trifluoromethyl)-phenyl)-3-(imidazo[1,2-b]pyridazin-3-ylethynyl)-4-methylbenzamide with a chloride compound to obtain N-(4-(chloromethyl)-3-(trifluoromethyl)phenyl)-3-(imidazo[1,2-b]pyridazin-3-ylethynyl)-4-methylbenzamide may include adding N-(4-(hydroxymethyl)-3-(trifluoromethyl) phenyl)-3-(imidazo[1,2-b]pyridazin-3-ylethynyl)-4-methylbenzamide to a solution of dimethylformamide (DMF) and $POCl_3$.

In yet still further embodiments, the N-(4-(hydroxymethyl)-3-(trifluoromethyl)-phenyl)-3-(imidazo[1,2-b]pyridazin-3-ylethynyl)-4-methylbenzamide may be obtained by a process which includes dissolving 4-(3-(imidazo[1,2-b]pyridazin-3-ylethynyl)-4-methylbenzamido)-2-(trifluoromethyl) benzyl acetate in a solvent and then adding a base. Suitable solvents include but are not limited to tetrahydrofuran (THF) and 2-methyl tetrahydrofuran (2-Me THF). In some embodiments the solvent is THF. Suitable bases include but are not limited to NaOH, KOH and LiOH. In some embodiments the base is NaOH.

In yet still further embodiments, the N-(4-(hydroxymethyl)-3-(trifluoromethyl)-phenyl)-3-(imidazo[1,2-b]pyridazin-3-ylethynyl)-4-methylbenzamide may be obtained by a process which includes dissolving N-(4-formyl-3-(trifluoromethyl)-phenyl)-3-(imidazo[1,2-b]pyridazin-3-ylethynyl)-4-methylbenzamide in a solvent and then adding sodium borohydride.

In accordance with other embodiments, the N-(4-(hydroxymethyl)-3-(trifluoromethyl) phenyl)-3-(imidazo[1,2-b]pyridazin-3-ylethynyl)-4-methylbenzamide may be obtained by a process including dissolving N-(4-(hydroxymethyl)-3-(trifluoromethyl) phenyl)-3-iodo-4-methylbenzamide in a solvent to form a solution, adding a base, an iodide reagent and a catalyst to the solution, and subsequently adding 3-ethynylimidazo[1,2-b] pyridazine to the solution. Suitable solvents for dissolving N-(4-(hydroxymethyl)-3-(trifluoromethyl) phenyl)-3-iodo-4-methylbenzamide include but are not limited to DMF and DMSO. In one embodiment the solvent is DMF. Suitable bases include but are not limited to DIPEA, TEA and DEA. In one embodiment the base is DIPEA. An exemplary suitable iodide reagent for addition to a solution of N-(4-(hydroxymethyl)-3-(trifluoromethyl) phenyl)-3-iodo-4-methylbenzamide is CuI.

Suitable catalysts for addition to a solution of N-(4-(hydroxymethyl)-3-(trifluoromethyl) phenyl)-3-iodo-4-methylbenzamide include but are not limited to $PdCl_2(PPh_3)_2$, $Pd(PPh_3)_4$, $Pd(dppe)Cl$, $Pd(dppp)Cl_2$, and $Pd(dppf)Cl_2$. In one embodiment the catalyst is $PdCl_2(PPh_3)_2$.

In yet further embodiments, the N-(4-(hydroxymethyl)-3-(trifluoromethyl) phenyl)-3-iodo-4-methylbenzamide may be obtained by a process which includes combining (4-amino-2-(trifluoromethyl) phenyl) methanol in dichloromethane and adding pyridine, and subsequently adding 3-iodo-4-methylbenzoyl chloride solution in dichloromethane.

Given above is a simplified summary in order to provide a basic understanding of some aspects described herein. This summary is not an extensive overview, and is not intended to identify key/critical elements or to delineate the scope of the claimed subject matter.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

The following description describes novel synthetic schemes which provide economical and easily scalable methods for making the drug ponatinib at a commercial scale.

The following embodiments of novel Schemes I-IV are provided.

SCHEME I

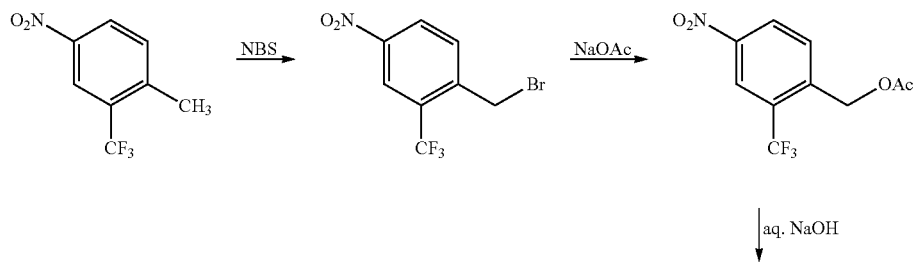

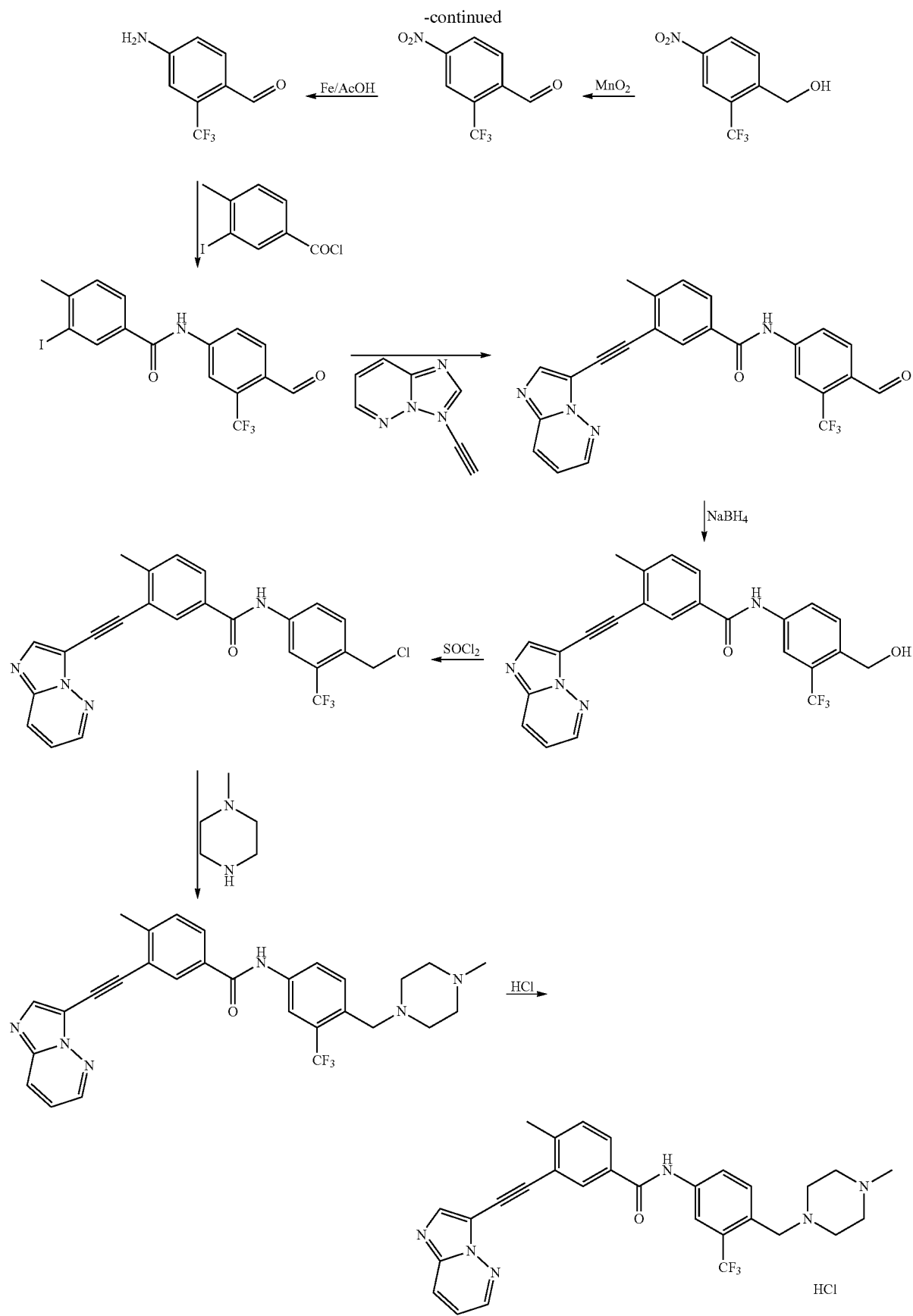

SCHEME II
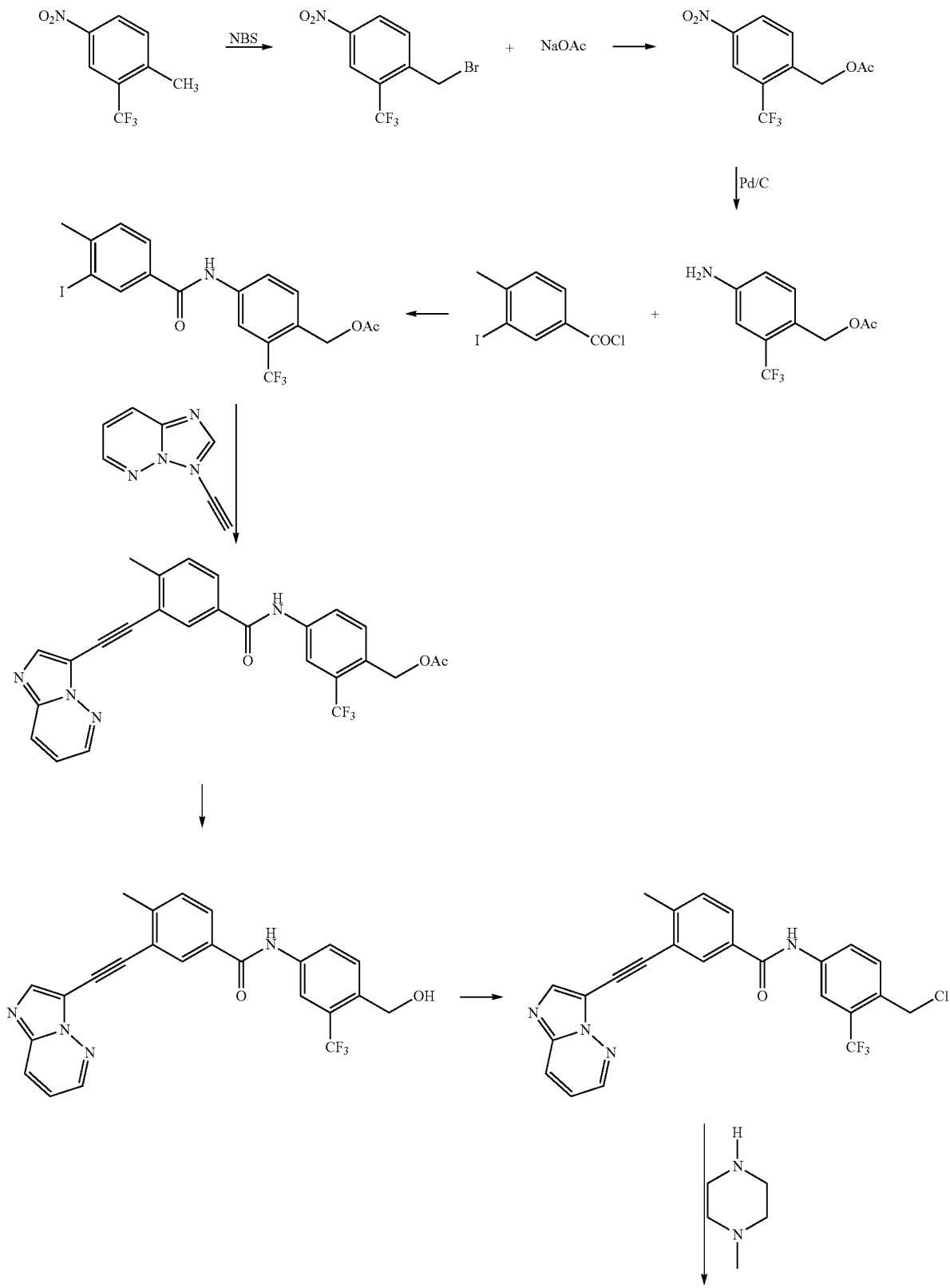

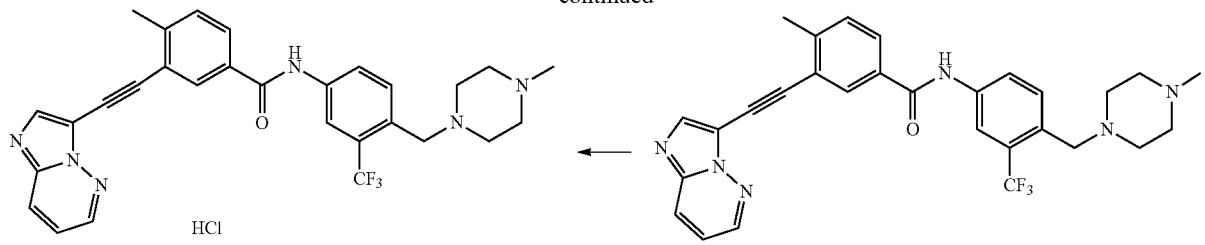

Examples and Experiments—Scheme II

Example 1
1-(Bromomethyl)-4-nitro-2-(trifluoromethyl)benzene

A suspension of 2-methyl-5-nitrobenzotrifluoride (3.90 g, 19 mmol), N-bromosuccinimide (NBS, 3.56 g, 20 mmol), 2,2'-azobis(2-methylpropionitrile) (AIBN, 94 mg, 0.6 mmol) in $CCl_4$ (40 mL) was refluxed under nitrogen for 16 h. HPLC indicated ca. 50% conversion. More NBS (10 mmol) and AIBN (0.6 mmol) were added, and the mixture was refluxed for another 14 h. HPLC indicated ca. 80% conversion. The reaction mixture was cooled down, and the solid was filtered off and washed with ethyl acetate. The combined filtrate was washed with aq. $NaHCO_3$, dried over $Na_2SO_4$, filtered, concentrated on rotovap and further dried under vacuum to afford a solid.

Example 2 4-Nitro-2-(trifluoromethyl)benzyl acetate

A suspension of 1-(Bromomethyl)-4-nitro-2-(trifluoromethyl)benzene (1 mmol), potassium acetate (1.2 mmol) in DMF was stirred at RT for 3 hr. After completion of the reaction, the reaction mixture was diluted with water and extracted in ethyl acetate thrice. The combined organic layer was washed with water, dried over $Na_2SO_4$, filtered, and evaporated on rotovap to afford yellow coloured viscous liquid.

Example 3 4-Amino-2-(trifluoromethyl)benzyl acetate

4-Nitro-2-(trifluoromethyl)benzyl acetate (1 mmol) was dissolved in AcOH. Iron powder (5 mmol) was added portionwise to the mixture. The reaction mixture was stirred at RT for 2-3 hrs. At the completion of the reaction pH of the reaction mass was adjusted up to 10-12 by adding sat. $Na_2CO_3$ solution at 0-10° C. and extracted with ethyl acetate thrice. The combined organic layer was washed with water, dried over $Na_2SO_4$, filtered, and evaporated on rotovap to obtain solid material.

Example 4 4-(3-Iodo-4-methylbenzamido)-2-(trifluoromethyl)benzyl acetate 4-amino-2-(trifluoromethyl)benzyl acetate (1 mmol) was dissolved in MDC. Triethylamine (1.5 mmol) was added to the mixture. The mixture was cooled to 0° C. Then, solution of 3-iodo-4-methylbenzoyl chloride in MDC was added drop wise to the mixture. Temperature was maintained at 0-5° C. during addition. The reaction mass was stirred at 0-10° C. for about 1 hr, and then at RT for half an hour. At the completion of the reaction the reaction mass was poured into water and stirred for about 20 min. Then the organic layer was separated, washed with saturated $Na_2CO_3$ solution on cooling, dried over $Na_2SO_4$, filtered, and evaporated on rotovap to obtain solid material.

Example 5 4-(3-(Imidazo[1,2-b]pyridazin-3-ylethynyl)-4-methylbenzamido)-2-(trifluoromethyl)benzyl acetate 4-(3-iodo-4-methylbenzamido)-2-(trifluoromethyl)benzyl acetate was dissolved in DMF, DIPEA, CuI and $Pd(PPh_3)_4$ were added and the mixture was stirred under nitrogen. The mixture was stirred for around 10-20 min., then 3-ethynylimidazo[1,2-b]pyridazine was added to the mixture. The reaction mixture was stirred at RT for about 2-3 hrs. under nitrogen. Reaction progress was monitored by TLC. At the completion of the reaction the reaction mass was poured into water and filtered. Then the residue was taken in methanol and stirred for 10 min. and filtered. Filtrate was evaporated under vacuum to obtain solid material.

Example 6 N-(4-(Hydroxymethyl)-3-(trifluoromethyl)-phenyl)-3-(imidazo[1,2-b]pyridazin-3-ylethynyl)-4-methylbenzamide 4-(3-(Imidazo[1,2-b]pyridazin-3-ylethynyl)-4-methylbenzamido)-2-(trifluoromethyl) benzyl acetate (1 mmol) was dissolved in THF (20 vol.) and then 1 M NaOH solution (16 mmol) was added thereto at RT. The reaction mixture was stirred for 2-3 hr and then diluted with ethyl acetate and the aq. layer extracted with ethyl acetate. Then organic layer was dried over $Na_2SO_4$, filtered, and evaporated on rotovap to obtain residue.

Example 7 N-(4-(Chloromethyl)-3-(trifluoromethyl) phenyl)-3-(imidazo[1,2-b]pyridazin-3-ylethynyl)-4-methylbenzamide N-(4-(hydroxymethyl)-3-(trifluoromethyl)-phenyl)-3-(imidazo[1,2-b]pyridazin-3-ylethynyl)-4-methylbenzamide (1 mmol) was taken in MDC, thionyl chloride (4 mmol) was added to it and the mixture was stirred for 3-4 hrs. At the completion of the reaction, solvent and thionyl chloride were evaporated under vacuum at 50-60° C. to obtain free solid material.

Example 8 3-(Imidazo[1,2-b]pyridazin-3-ylethynyl)-4-methyl-N-(4-((4-methylpiperazin-1-yl)methyl)-3-(trifluoromethyl)phenyl)benzamide N-(4-(chloromethyl)-3-(trifluoromethyl)phenyl)-3-(imidazo[1,2-b]pyridazin-3-ylethynyl)-4-methylbenzamide (1 mmol) was taken in MDC, N-methylpiperazine (1.2 mmol) was added and the mixture was stirred for about 3-4 hrs. At the completion of the reaction the reaction mass was poured into water and extracted with MDC. The organic layer was separated, dried with anhydrous sodium sulphate and evaporated to obtain solid material.

Example 9 3-(Imidazo[1,2-b]pyridazin-3-ylethynyl)-4-methyl-N-(4-((4-methylpiperazin-1-yl)methyl)-3-(trifluoromethyl)phenyl)benzamide hydrochloride 3-(Imidazo[1,2-b]pyridazin-3-ylethynyl)-4-methyl-N-(4-((4-methylpiperazin-1-yl)methyl)-3-(trifluoromethyl)phenyl)benzamide (1 mmol) was dissolved in methanol (5 vol.) and saturated with HCl gas at 0-5° C. and stirred for 1-2 hrs. The solid was filtered, washed with methanol, suction dried and dried at 50-60° C. to obtain hydrochloride salt.

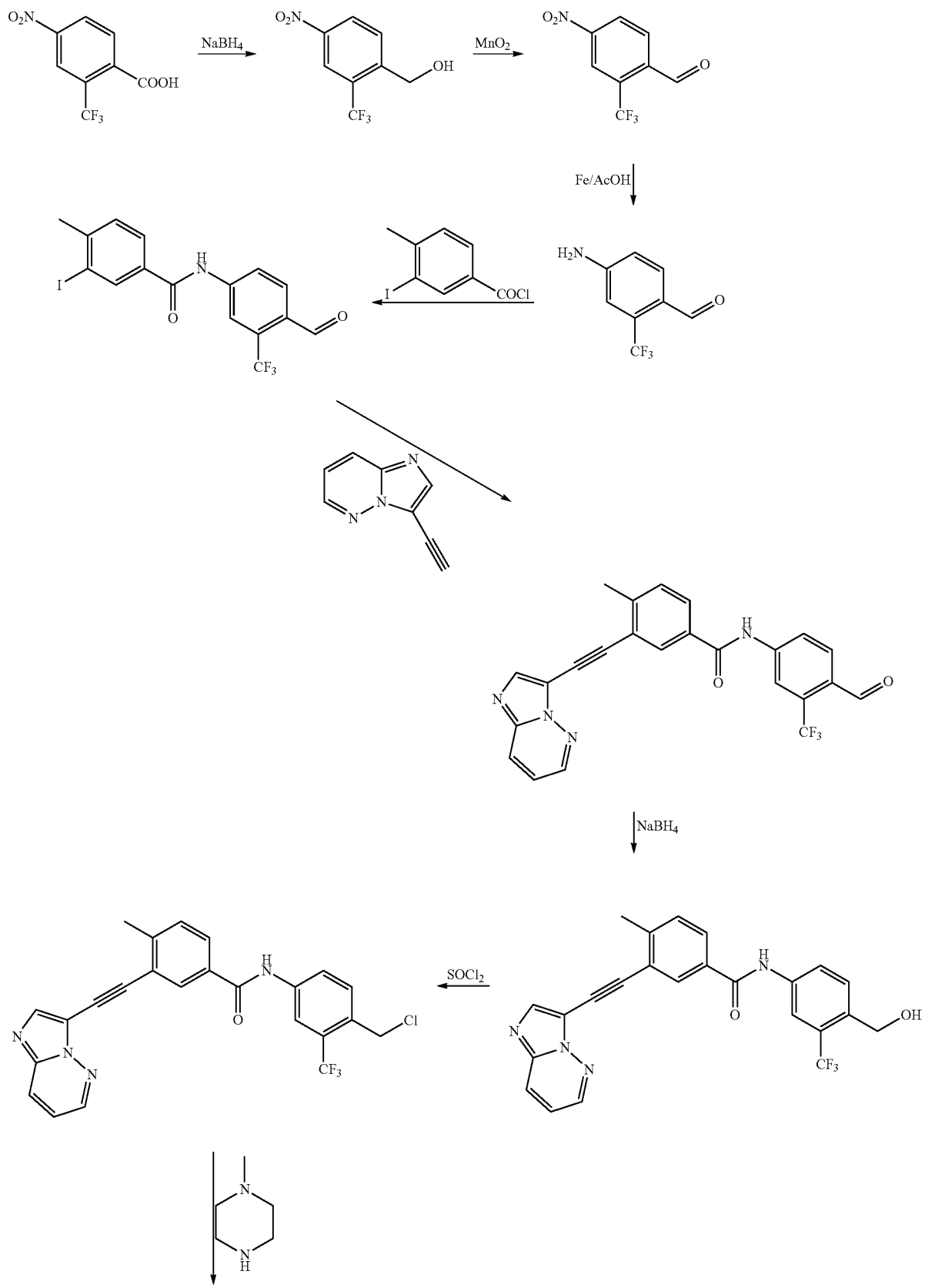
SCHEME III

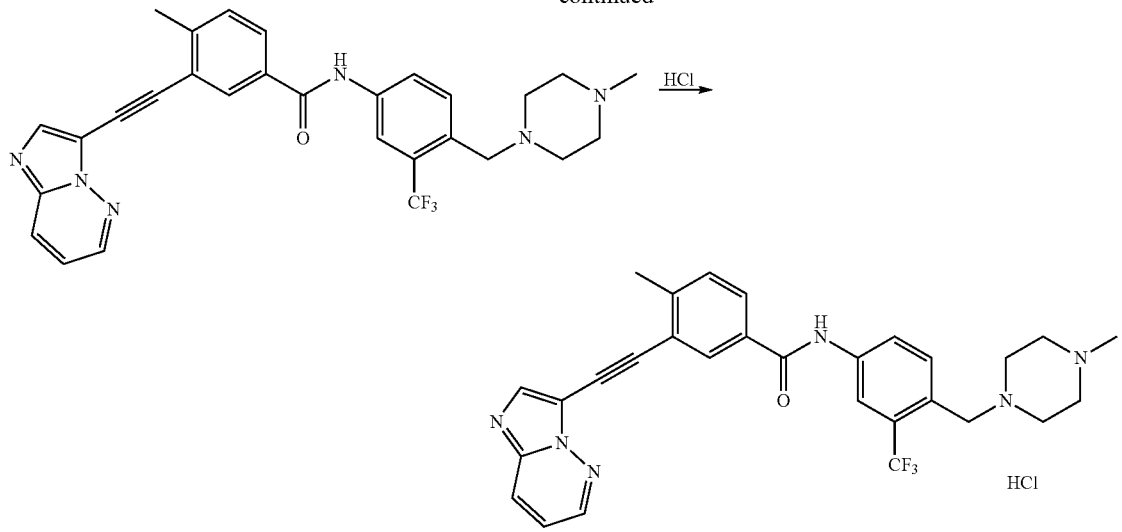

Examples and Experiments—Schemes I and III

Example 10
(4-Nitro-2-(trifluoromethyl)phenyl)methanol

4-Nitro-2-(trifluoromethyl) benzoic acid (1 mmol) was taken up in THF (10 vol.) and NaBH$_4$ (2.95 mmol) was added portionwise. The reaction mixture was cooled to 0-10° C., then boron trifluoride etherate (2.84 mmol) was added dropwise and the mixture stirred overnight at RT. The mixture was cooled to 0° C. and combined with 1 M NaOH solution with stirring. Then THF was evaporated and the crude product was extracted with ethyl acetate. The organic layer was washed with sat. NaCl solution, dried on Na$_2$SO$_4$, filtered, and evaporated to obtain the residue.

Example 11
4-Nitro-2-(trifluoromethyl)benzaldehyde

A suspension of (4-Nitro-2-(trifluoromethyl)phenyl) methanol (1 mmol), MnO$_2$ (10 wt) in CHCl$_3$ was refluxed for 3-4 hrs. At the completion of the reaction, the reaction mass was filtered, filtrate was evaporated to dryness.

Example 12
4-Amino-2-(trifluoromethyl)benzaldehyde

4-Nitro-2-(trifluoromethyl)benzaldehyde (1 mmol) was dissolved in AcOH. Iron powder (5 mmol) was added portionwise to the mixture. The reaction mixture was stirred at RT for 2-3 hrs. At the completion of the reaction pH of the reaction mass was adjusted up to 10-12 by adding sat. Na$_2$CO$_3$ solution at 0-10° C. and extracted with ethyl acetate thrice. The combined organic layer was washed with water, dried over Na$_2$SO$_4$, filtered, and evaporated on rotovap to obtain solid material.

Example 13 N-(4-Formyl-3-(trifluoromethyl)phenyl)-3-iodo-4-methylbenzamide

4-Amino-2-(trifluoromethyl)benzaldehyde (1 mmol) was dissolved in MDC, and triethylamine (1.5 mmol) was added to it. The mixture was cooled to 15-25° C. Then, a solution of 3-iodo-4-methylbenzoyl chloride in MDC was added drop-wise to the mixture. Temperature was maintained at 15-25° C. during addition. The reaction mass was stirred at 15-25° C. for about 1 hr. and then at RT for half an hour. At the completion of the reaction the reaction mass was poured into water and stirred for about 20 min. Then the organic layer was separated, washed with sat. Na$_2$CO$_3$ solution on cooling, dried over Na$_2$SO$_4$, filtered, and evaporated on rotovap to obtain solid material.

Example 14 N-(4-Formyl-3-(trifluoromethyl)-phenyl)-3-(imidazo[1,2-b]pyridazin-3-ylethynyl)-4-methylbenzamide N-(4-formyl-3-(trifluoromethyl)phenyl)-3-iodo-4-methylbenzamide (1 mmol) was dissolved in DMF, DIPEA, CuI and PdCl2(PPh3)2 were added to the mixture and the mixture was stirred under nitrogen for around 10-20 min. Then 3-ethynylimidazo[1,2-b]pyridazine (2 mmol) was added to the mixture. The reaction mixture was stirred at RT for about 2-3 hrs. under nitrogen. Reaction progress was monitored by TLC. At the completion of the reaction the reaction mass was poured into water and filtered. Then the residue (filter cake) was taken in methanol and stirred for 10 min. and filtered. Filtrate was evaporated under vacuum to obtain solid material.

Example 15 N-(4-(Hydroxymethyl)-3-(trifluoromethyl)-phenyl)-3-(imidazo[1,2-b]pyridazin-3-ylethynyl)-4-methylbenzamide N-(4-formyl-3-(trifluoromethyl)-phenyl)-3-(imidazo[1,2-b]pyridazin-3-ylethynyl)-4-methylbenzamide (1 mmol) was dissolved in ethanol and then sodium borohydride (0.3 mmol) was added to it at 0-5° C. The reaction mixture was stirred at 0-5° C. for 2-3 hr and then at RT for half an hour. At the completion of the reaction the reaction mass was poured into water. White coloured solids precipitated out were filtered, washed with water and dried under vacuum.

Example 16 N-(4-(Chloromethyl)-3-(trifluoromethyl)phenyl)-3-(imidazo[1,2-b]pyridazin-3-ylethynyl)-4-methylbenzamide N-(4-(hydroxymethyl)-3-(trifluoromethyl)-phenyl)-3-(imidazo[1,2-b]pyridazin-3-ylethynyl)-4-methylbenzamide (1 mmol) was taken in MDC, thionyl chloride (4 mmol) was added to it at 25-30° C. and the mixture was stirred for 3-4 hrs. At the completion of the reaction, solvent and thionyl chloride were evaporated under vacuum at 50-60° C. to obtain free solid material.

Example 17 3-(Imidazo[1,2-b]pyridazin-3-ylethynyl)-4-methyl-N-(4-((4-methylpiperazin-1-yl)methyl)-3-(trifluoromethyl)phenyl)benzamide N-(4-(chloromethyl)-3-(trifluoromethyl)phenyl)-3-(imidazo[1,2-b]pyridazin-3-ylethynyl)-4-methylbenzamide (1 mmol) was taken in MDC, N-methylpiperazine (1.2 mmol) was added to the mixture and the mixture was stirred for about 3-4 hrs. At the completion of the reaction the reaction mass was poured into water and extracted with MDC. The organic layer was separated, dried with anhydrous sodium sulphate and evaporated to obtain solid material.

Example 18 3-(Imidazo[1,2-b] pyridazin-3-ylethynyl)-4-methyl-N-(4-((4-methylpiperazin-1-yl) methyl)-3-(trifluoromethyl)phenyl)benzamide hydrochloride 3-(Imidazo[1,2-b] pyridazin-3-ylethynyl)-4-methyl-N-(4-((4-methylpiperazin-1-yl) methyl)-3-(trifluoromethyl) phenyl) benzamide (1 mmol) was dissolved in methanol (5 vol.) and saturated with HCl gas at 0-5° C. and stirred for 1-2 hrs. The solid was filtered, washed with methanol, suction dried and dried at 50-60° C. to obtain the hydrochloride salt.

SCHEME IV

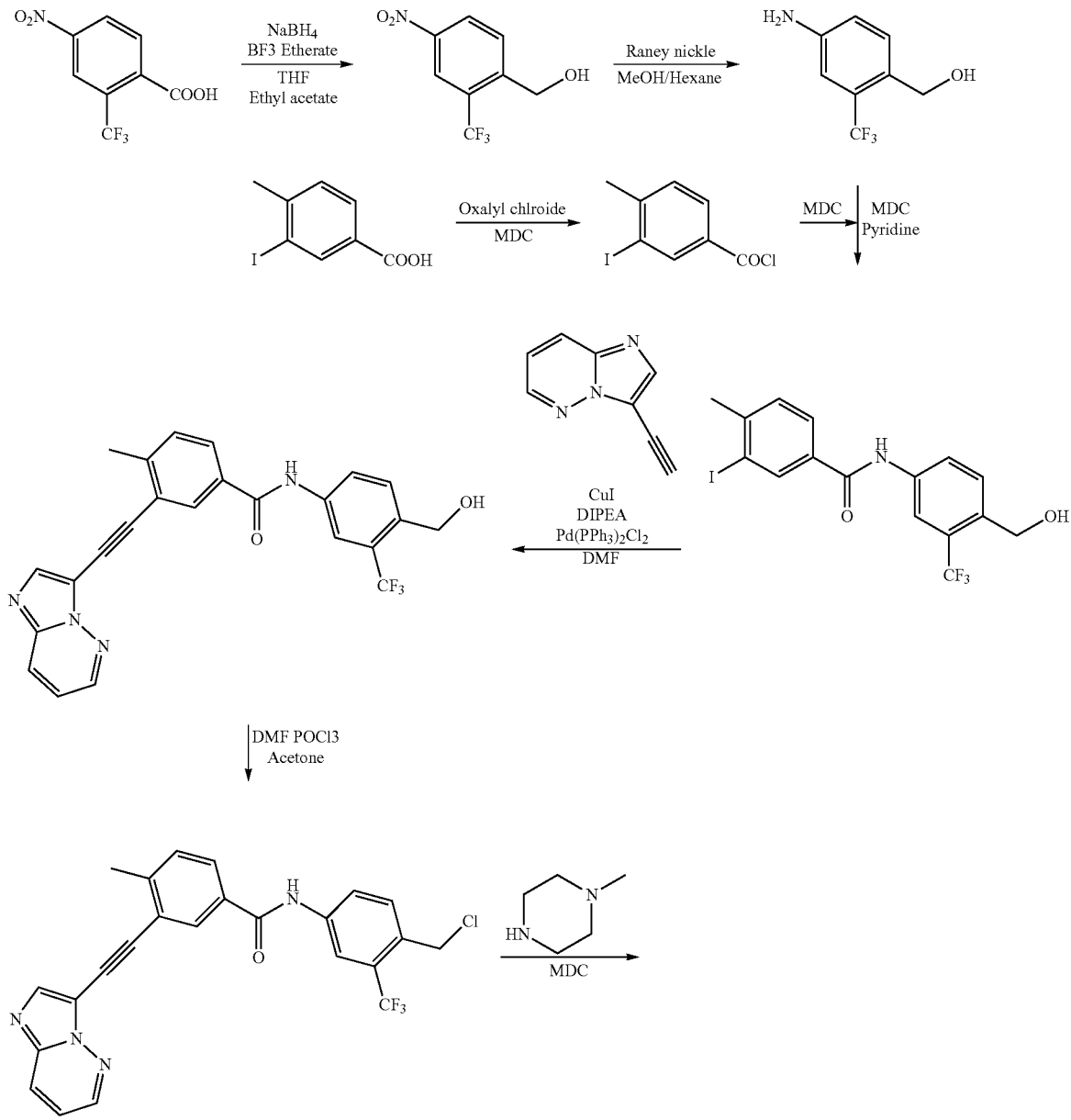

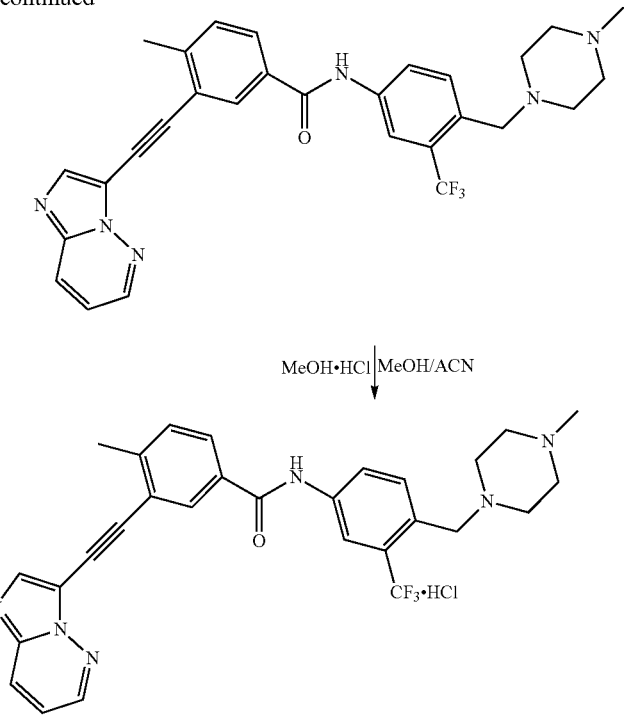

MeOH•HCl | MeOH/ACN

Examples and Experiments—Scheme IV

Example 19
(4-Nitro-2-(trifluoromethyl)phenyl)methanol

4-Nitro-2-(trifluoromethyl) benzoic acid (1 mmol) was taken up in THF (10 vol.) and NaBH4 (2.95 mmol) was added portion wise. The reaction mixture was cooled to 0-10° C., then boron difluoride etherate (2.84 mmol) was added dropwise and the mixture stirred overnight at RT. The mixture was cooled to 0° C. and combined with 1 M NaOH solution with stirring. Then THF was evaporated and the crude product was extracted with ethyl acetate. The organic layer was washed with sat. NaCl solution, dried on $Na_2SO_4$, filtered, and evaporated to obtain the residue.

Example 20 (4-amino-2-(trifluoromethyl) phenyl)methanol

A suspension of (4-Nitro-2-(trifluoromethyl) phenyl) methanol (1 mmol), Raney nickel (30% wet) in methanol was refluxed for 3-4 hrs. At the completion of the reaction, the reaction mass was filtered through celite and the filtrate concentrated to a thick mass, and subsequently the solid was crystallized using hexane.

Example 21 3-Iodo-4-methylbenzoyl chloride

3-Iodo-4-methylbenzoic acid (1 mmol) was dissolved in dichloromethane and then oxalyl chloride charged in the vessel at 0 to 5°. A catalytic amount of dimethylformamide was charged in the vessel. The reaction mass temperature was raised to 25-30° C. and maintained for 16-18 hrs. After completion of the reaction, the reaction mass was distilled to a thick oily mass which was subsequently used for further reaction.

Example 22 N-(4-(hydroxymethyl)-3-(trifluoromethyl)phenyl)-3-iodo-4-methylbenzamide (4-amino-2-(trifluoromethyl) phenyl) methanol (1 mmol) was taken in dichloromethane & then pyridine (3 mmol) was added to obtain a clear solution. Then was added 3-iodo-4-methylbenzoyl chloride solution in dichloromethane slowly at 0-5° C. The reaction was allowed to come at 25-30° C., and maintained for 2-3 hrs. After completion of reaction, the product was isolated as a solid after addition of water to the reaction mass.

Example 23 N-(4-(hydroxymethyl)-3-(trifluoromethyl)phenyl)-3-(imidazo[1,2-b]pyridazin-3-ylethynyl)-4-methylbenzamide N-(4-(hydroxymethyl)-3-(trifluoromethyl) phenyl)-3-iodo-4-methylbenzamide (1 mmol) was dissolved in DMF, DIPEA, CuI and $PdCl_2(PPh_3)_2$ were added to the mixture and the mixture was stirred under nitrogen for around 10-20 min., then 3-ethynylimidazo[1,2-b] pyridazine (2 mmol) was added to the mixture. The reaction mixture was stirred at RT for about 2-3 hrs. under nitrogen. Reaction progress was monitored by TLC. At the completion of the reaction the reaction mass was poured into water and filtered. Then the residue (filter cake) was purified from acetonitrile to get the solid product.

Example 24 N-(4-(chloromethyl)-3-(trifluoromethyl)phenyl)-3-(imidazo[1,2-b]pyridazin-3-ylethynyl)-4-methylbenzamide N-(4-(hydroxymethyl)-3-(trifluoromethyl) phenyl)-3-(imidazo [1,2-b] pyridazin-3-ylethynyl)-4-methylbenzamide (1 mmol) was charged to a solution of dimethylformamide & $POCl_3$ (Vilsmeier reagent) slowly at 0-5° C. and maintained for 4-5 hrs at 25-30° C. After completion of reaction, the reaction mass was charged to process water to get solid product. This solid product was purified in methanolic HCl as HCl salt, which was subsequently used for further stages.

Example 25 3-(Imidazo[1,2-b]pyridazin-3-ylethynyl)-4-methyl-N-(4-((4-methylpiperazin-1-yl)methyl)-3-(trifluoromethyl)phenyl)benzamide N-(4-(chloromethyl)-3-(trifluoromethyl) phenyl)-3-(imidazo[1,2-b] pyridazin-3-ylethynyl)-4-methylbenzamide (1 mmol) was taken in dichloromethane (30.0 volumes). N-methylpiperazine (3.0 volumes) was added to the mixture and the mixture was stirred for about 10-12 hrs. At the completion of the reaction the reaction mass was quenched by adding a saturated solution of sodium bicarbonate. The organic layer washed with process water and further treated with charcoal and dried over sodium sulphate. Finally, the organic layer was evaporated to dryness to get solid product as ponatinib base (ponatinib technical).

Example 26 3-(Imidazo[1,2-b]pyridazin-3-ylethynyl)-4-methyl-N-(4-((4-methylpiperazin-1-yl)methyl)-3-(trifluoromethyl)phenyl)benzamide hydrochloride 3-(Imidazo[1,2-b]pyridazin-3-ylethynyl)-4-methyl-N-(4-((4-methylpiperazin-1-yl)methyl)-3-(trifluoromethyl)phenyl)benzamide (1 mmol) was charged to methanol (4.0 volumes) and acetonitrile (1.0 volume) and then methanolic HCl solution was slowly added by adjusting pH of reaction mass to 4.0-4.5 to get the desired monohydrochloride. The reaction mass was seeded with the desired polymorph Form-I and then degassed to reduce the excess acidity. Finally the product was isolated after filtration. The solid was dried at 50-55° C. under vacuum 720-750 mm of Hg to get residual solvents as per ICH limits. This process overcomes the earlier prior art processes of making Form-I in which the residual solvents are always seen above the limits.

Although the compositions and methods of the present disclosure have been described with reference to exemplary embodiments thereof, the present disclosure is not limited thereby. Indeed, the exemplary embodiments are implementations of the disclosed compositions and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A method of making ponatinib or a pharmaceutically acceptable salt thereof, comprising the steps of:
   reacting 3-iodo-4-methylbenzoyl chloride with a solution of 4-amino-2-(trifluoromethyl)benzaldehyde to obtain N-(4-formyl-3-(trifluoromethyl)phenyl)-3-iodo-4-methylbenzamide;
   adding a base, an iodide reagent and a catalyst to a solution of N-(4-formyl-3-(trifluoromethyl)phenyl)-3-iodo-4-methylbenzamide to obtain a reaction mixture, and adding 3-ethynylimidazo[1,2-b]pyridazine to the reaction mixture to obtain N-(4-formyl-3-(trifluoromethyl)-phenyl)-3-(imidazo[1,2-b]pyridazin-3-ylethynyl)-4-methylbenzamide;
   reacting a solution of N-(4-formyl-3-(trifluoromethyl)-phenyl)-3-(imidazo[1,2-b]pyridazin-3-ylethynyl)-4-methylbenzamide with sodium borohydride to obtain N-(4-(hydroxymethyl)-3-(trifluoromethyl)-phenyl)-3-(imidazo[1,2-b]pyridazin-3-ylethynyl)-4-methylbenzamide;
   reacting a solution of N-(4-(hydroxymethyl)-3-(trifluoromethyl)-phenyl)-3-(imidazo[1,2-b]pyridazin-3-ylethynyl)-4-methylbenzamide with a chloride compound to obtain N-(4-(chloromethyl)-3-(trifluoromethyl)phenyl)-3-(imidazo[1,2-b]pyridazin-3-ylethynyl)-4-methylbenzamide; and
   reacting a solution of N-(4-(chloromethyl)-3-(trifluoromethyl)phenyl)-3-(imidazo[1,2-b]pyridazin-3-ylethynyl)-4-methylbenzamide with N-methylpiperazine to obtain 3-(imidazo[1,2-b]pyridazin-3-ylethynyl)-4-methyl-N-(4-((4-methylpiperazin-1-yl)methyl)-3-(trifluoromethyl)phenyl)benzamide.

2. The method of claim 1 comprising the further step of saturating a solution of the 3-(imidazo[1,2-b]pyridazin-3-ylethynyl)-4-methyl-N-(4-((4-methylpiperazin-1-yl)methyl)-3-(trifluoromethyl)phenyl)benzamide with HCl gas to form ponatinib hydrochloride.

3. The method of claim 1 wherein the base is selected from the group consisting of N,N-diisopropylethylamine (DIPEA), triethyl amine (TEA) and diethylamine (DEA).

4. The method of claim 1 wherein the iodide reagent is CuI.

5. The method of claim 1 wherein the catalyst is selected from the group consisting of $PdCl_2(PPh_3)_2$, $Pd(PPh_3)_4$, Pd(dppe)Cl, $Pd(dppp)Cl_2$, and $Pd(dppf)Cl_2$.

6. The method of claim 1 wherein the chloride is selected from the group consisting of phosphoryl chloride, thionyl chloride, oxalyl chloride, cyanuric chloride and phosphorous pentachloride.

7. The method of claim 1 wherein the 4-amino-2-(trifluoromethyl) benzaldehyde is obtained by reacting a solution of 4-nitro-2-(trifluoromethyl)benzaldehyde in AcOH with iron.

* * * * *